United States Patent [19]

Lawrence, Jr. et al.

[11] 4,381,624

[45] May 3, 1983

[54] HIGH PURITY HYBRID CABBAGE SEED PRODUCTION

[75] Inventors: Robert H. Lawrence, Jr., Tarrytown, N.Y.; Phillip E. Hill, Hollister, Calif.

[73] Assignee: Agrigenetics Research Associates Limited, Denver, Colo.

[21] Appl. No.: 169,875

[22] Filed: Jul. 17, 1980

[51] Int. Cl.³ .............................................. A01G 1/00
[52] U.S. Cl. .................................... 47/58; 47/DIG. 1
[58] Field of Search .............................. 47/58, DIG. 1

[56] References Cited

U.S. PATENT DOCUMENTS

| | | | |
|---|---|---|---|
| 2,258,291 | 10/1971 | Jones | 47/58 |
| 2,522,409 | 9/1950 | Stoller | 71/2.1 |
| 2,747,334 | 5/1956 | Routinen et al. | 47/58 |
| 3,009,289 | 11/1961 | Tukacs | 47/1 |
| 3,514,900 | 6/1970 | McDade | 47/58 |
| 3,683,550 | 8/1972 | Corlett, Jr. et al. | 47/58 |
| 3,816,960 | 6/1974 | Gudin et al. | 47/58 |
| 3,821,864 | 7/1974 | Stottlemyer | 47/58 |
| 3,832,801 | 9/1974 | Carlson et al. | 47/58 |
| 3,846,937 | 11/1974 | Staba et al. | 47/58 |
| 3,861,079 | 1/1975 | Patterson | 47/58 |
| 3,955,317 | 5/1976 | Gudin | 47/1.2 |
| 3,972,146 | 8/1976 | Boxus | 47/58 |
| 4,003,315 | 1/1977 | Sibi | 47/58 |
| 4,038,778 | 8/1977 | Kadkade | 47/58 |
| 4,045,912 | 9/1977 | Sun | 47/58 |
| 4,052,817 | 10/1977 | Seibert | 47/58 |
| 4,060,933 | 12/1977 | Kadkade | 47/58 |

FOREIGN PATENT DOCUMENTS 1387821 3/1975 United Kingdom .

OTHER PUBLICATIONS

Encyclopedia Britannica, Macropedia, section on Tissue Culture, pp. 438–442.
Encyclopedia Britannica, Macropedia, section on Horticulture, pp. 1105–1114.
Encyclopedia Britannica, Macropedia, section on Plant Breeding, pp. 497–500.
Encyclopedia Britannica, Macropedia, section on Fruits & Farming, pp. 761–763.
Encyclopedia Britannica, Macropedia, section on Tissues and Fluids, Plant, pp. 451–455.
Encyclopedia Britannica, Macropedia, section on Vegetables & Vegetable Farming, pp. 43–52.
Anderson et al., "Tissue Culture Propagation of Broccoli", J.A.S. Hort. Science, 102(1), 69 (Jan. 1977).
Benson et al., "Meet U.C. 157," Am. Vegetable Grower, 8, May, 1978.
Yang, "Send in the Clones," Am. Veg. Grower, 8, Oct. 1978.

*Primary Examiner*—Robert E. Bagwill
*Attorney, Agent, or Firm*—Pennie & Edmonds

[57] ABSTRACT

A process for commercially producing high purity hybrid cabbage seed. One (or both) of the parental lines is rendered sib-incompatible by cloning a maximally self-incompatible parent plant so that the resulting line (or lines), consisting of cloned plants, is sib-as well as self-incompatible. The two parental lines, one or both of which is clonally derived, may then be crossed by natural pollination without encountering inbreeding of the cloned parental line (or lines). Prior difficulties in maintaining the parental inbred breeding lines are eliminated.

2 Claims, No Drawings

HIGH PURITY HYBRID CABBAGE SEED PRODUCTION

BACKGROUND OF THE INVENTION

This invention relates to the production of high purity hybrid cabbage seeds, and more particularly concerns a method of producing high purity $F_1$ hybrid cabbage seeds in high yield without the prior necessity of labor-intensive bud pollination to produce the parent plants or lines.

The current procedures used to produce $F_1$ hybrid cabbage seeds are widely recognized as having serious limitations, both in terms of cost and as regards seed purity. They all require the establishment and provision of stable, sib-incompatible, nearly homozygous, parental breeding lines, which are available after repeatedly selfing each genotype. Because cabbage are strongly self-incompatible (an individual plant will not readily pollinate with itself), inbreeding to maintain the parental lines can only be effected by bud pollination; each flower bud is opened by hand, and then pollinated from another flower on the same plant, again by hand.

These difficulties in maintaining the parental inbred breeding lines are reflected not only in high hybrid seed cost as a result of the labor cost, but, in practical effect, have required that the breeding lines be maintained in foreign low-labor-cost countries.

Moreover, the parental lines are of necessity highly inbred, and the plants have low vigor, resulting in low $F_1$ hybrid seed yields.

When making hybrid seed from two parental lines, either of two approaches are used. For one, the flowers in one line are emasculated by hand, and are fertilized with pollen from the crossing line. This manifestly is labor intensive, and consequently expensive. A second approach, widely used on a commercial scale, avoids emasculation. Two inbred parental lines, where one or both lines is sib-incompatible (does not readily pollinate with its siblings) as well as self-incompatible (nearly incapable of fertilizing itself) are crossed by natural pollination. Hybrid seed is collected only from the sib-incompatible breeding line. In the usual case, where one inbred is sib-incompatible, a high ratio, typically 3:1, of the sib-incompatible inbred to the normal inbred is used, and only the seed produced on the sib-incompatible inbred is harvested for sale. Ideally, if both inbreds are sib-incompatible, a 1:1 ratio of the two can be used, and, due to the reciprocity rule of genetics, the entire seed crop can be harvested.

While the sib-incompatible technique for $F_1$ hybrid cabbage seed production avoids many of the difficulties of emasculation, a number of problems are encountered in practice. One such problem is that large populations of inbreds are used, and these tend to drift genetically due to their being sexually reproduced.

An especially serious seed quality problem arises with the use of sib-incompatible hybrid techniques. If a "misnick" (poor timing between the two inbreds in their going into inflorescence) occurs, some sibbing takes place on the ostensibly sib-incompatible parent, giving rise to inbreds being present in the seed crop. This may result in the seed not being of sufficiently high purity to comply with present day labeling laws, which mandate that a hybrid seed contain at least 95% of the designated hybrid whereas self-incompatibility, being the stronger reaction, greatly reduces this problem.

And finally, the development of a sib-incompatible inbred normally requires at least about 10 years of inbreeding.

Accordingly, an object of the invention is to provide a method of commercially producing high purity cabbage seed while avoiding the prior difficulties of maintaining inbred parental breeding lines.

Another object is to provide such seed without requiring labor-intensive bud pollination.

Still another object is to provide a method for producing high purity hybrid cabbage seeds which combines the low labor cost of the sib-incompatible hybrid technique with nearly the seed purity of the manual emasculation technique.

Still a further object is to provide a method of making high purity hybrid cabbage seed without requiring the elaborate and expensive maintenance of self-incompatible, homozygous, parental breeding lines.

Another object is to maintain consistently high purity, and consistently high quality of hybrid cabbage seed, giving a better, constant quality product to the customer year in and year out.

Still another object is to provide a method for commercially producing hybrid cabbage seed while retaining local control of the inbred breeding lines.

Yet another object is to avoid the genetic drift associated with sexual propagation techniques for maintaining the breeding lines, and therefore to have higher quality commercial seed production.

An overall object is to provide a method for economically and rapidly producing high purity hybrid cabbage seed.

Briefly, in accordance with the invention, high purity hybrid cabbage seed is produced commercially by natural cross pollination of two parental breeding lines, one (or both) of which is rendered sib-incompatible by cloning a maximally self-incompatible individual parent plant. The prior need for inbreeding is avoided by selecting for the cloning a plant which exhibits the maximum degree of self-incompatibility, thereby producing clones of that plant which retain the high self-incompatibility. Thus, because the original parental plants are chosen for being self-incompatible, the clones are each the "self," and thus the clones are effectively sib-incompatible also.

Consequently, when one cloned parental line is naturally cross-pollinated with another parental line, only pollen from the latter can fertilize the first line. As a result, seed from the first line is of a uniformly high hybrid purity, with little or no likelihood of self-fertilization (inbreeding). If both of the parental lines are cloned parents, each selected for being maximally self-incompatible, then natural cross pollination of the two lines gives a seed crop obtainable from both lines.

The cloning technique has a major advantage over pre-existing methods of making hybrid seed. It eliminates the need for the elaborate and expensive procedures for establishing and maintaining sib-incompatible, nearly homozygous, parental breeding lines, which heretofore have required laborious manual bud pollination. By cloning optimal parents, the clones retain the optimum genetic characteristics of the parents. Further, when the cloning is effected according to the optimum practice of the present invention, the original-parent-derived hybrids are genetically equivalent to the cloned-parent-derived hybrids.

The cloning techniques prepared for use herein are similar to those developed for other purposes or for other plant species. See Encyclopaedia Britannica, Macropedia, "Tissue Culture," "Tissues and Fluids, Plant," "Horticulture, Plant Breeding," "Fruits and Fruit Farming," and "Vegetables and Vegetable Farming," together with articles cited therein. State-of-the-art technology is reviewed in "Propagation of Higher Plants Through Tissue Culture," Proceedings of International Symposium, University of Tennessee, Knoxville, Apr. 16–19, 1978 (Technical Information Center, U.S. Department of Energy, National Technical Information Service, U.S. Department of Commerce, Springfield, Virginia 22161, Conference T-80411); E. Thomas and M. R. Davey, "From Single Cells to Plants," (Wykenham Publ. 1975); and D. N. Butcher and D. S. Ingram, "Plant Tissue Culture," (Camelot Press, 1976). A pertinent literature reference is W. C. Anderson and J. B. Carstens, "Tissue Culture Propagation of Broccoli, Brassica oleracea (Italica Group) for use in $F_1$ Hybrid Seed Production," J. Am. Soc. Hort. Sci., 102(1), 69–73 (1977), and references cited therein, together with references in the Example below. Patent references include Kadkade U.S. Pat. No. 4,038,778, McCormick Brit. Pat. No. 1,387,821, Sibi U.S. Pat. No. 4,003,156, Routien U.S. Pat. No. 2,747,334, Tukacs U.S. Pat. No. 3,009,289, McDade U.S. Pat. No. 3,514,900, Corlett U.S. Pat. No. 3,683,550, Gudin U.S. Pat. No. 3,816,960, Stottlemeyer U.S. Pat. No. 3,821,864, Carlson U.S. Pat. No. 3,832,801, Patterson U.S. Pat. No. 3,861,079, Gudin U.S. Pat. No. 3,955,317, Boxus U.S. Pat. No. 3,972,146, Seibert U.S. Pat. No. 4,052,817, and Kadkade U.S. Pat. No. 4,060,933.

SCHEDULE

A typical schedule for the commercial production in California of high purity hybrid cabbage seed is presented below. Individual operations conducted according to the schedule are also discussed.

(1) Summer, first year

In the summer of the first year, a row of about 50 feet of each inbred parental line (genotype) used in making the selected hybrid is sown. These will be thinned. Conventional farming practices are followed and the plants in each parental line are permitted to grow to full market maturity.

(2) Fall, first year

In the fall of the first year, when the plants have reached market maturity, about ten plants from each parental line are selected for their morphological characteristics. The individual plants are labeled, as by physically tagging the plant. Each of the selected plants is then prepared for transplanting by trimming to a stump. When the plants have regrown, they are lifted and individually potted, and then moved to the greenhouse.

When the individual plants are selected, explants of each of the ten plants are taken for vegetative cloning. The cloning procedure, detailed below, is conducted organogenetically, under suitable tissue growth conditions in an aseptic nutrient medium. Alternatively, some of the explants may be stored, as for example under cryogenic conditions, e.g., Seibert U.S. Pat. No. 4,052,817.

(3) Spring, second year

Each of the selected plants blooms from March through April. Standard horticultural test procedures for determining maximum self-incompatibility are applied to identify the individuals in each line that have the strongest self-incompatibility. The test, in substance, involves growing each of the plants to maturity without external pollination, and then determining which plants produce the smallest yield of seeds, indicating the highest resistance to self-pollination (self-incompatibility). The results of these tests are available by mid-July of the second year.

(4) Summer, second year

Based on the tests used to determine which individual plants of each parental line have the strongest self-incompatibility, an individual plant is selected within each parental line.

Explants previously taken from each of the two selected individuals that exhibited maximum self-incompatibility are vegetatively propagated, as set forth below, to provide about 50 clones of each plant. Propagation of explants from the non-selected plants are discontinued as soon as the selection has been made.

(5) Fall, second year

The regenerated clones are transplanted in the fall of the second year, and are crossed to make cloned-parent-derived hybrids on a pilot production scale.

The clones are planted so that the cloned parental lines are in close proximity to each other but are isolated from chance fertilization by pollen from extraneous plants. Crossing of the lines occurs by natural pollination. This is best effected in large cages screened to exclude extraneous insects, but permitting flies, bees, or other insects contained within the cages to cross-pollinate the parental lines.

(6) Fall, third year

By the fall of the third year, hybrid seed from the crossing of cloned parents is harvested. Some seed from the cloned-parent-derived hybrids is then sent to an appropriate climate, e.g., Florida, for planting. The resulting cloned-parent-derived hybrid cabbage may then be compared with original-parent-derived hybrid cabbage made by crossing (by bud pollination) the two selected individual parent plants.

(7) Spring, fourth year

Some cloned-parent-derived hybrid seed from the pilot production, along with the original-parent-derived hybrid seed, is sown in California to verify that the cloned-parent-derived hybrids are equivalent to the original-parent-derived hybrids.

(8) Summer, fourth year

Upon verification that the cloned-parent derived hybrids are genetically comparable to the original-parent-derived hybrids, production plans can be made for using the clones in large scale production of $F_1$ hybrid seed.

Additional clones are prepared by tissue culture technique, this time on a large scale suitable for commercial production. Procedures for cloning are set out below.

(9) Fall, fourth year

In the fall of the fourth year, the commercial hybrid production fields are set out. A plant density of about 8,000 plants per acre is used, and an equal number of plants from each of the parent lines is used. These are then naturally cross-pollinated by insects. Seed from these plants is harvested, and is ready for sale. As indicated previously, since each of the cloned parent lines is sib-incompatible, and since the reciprocal crosses have been tested for genetic equivalency, the entire seed production is marketable.

VEGETATIVE PROPAGATION OF INBREDS

The technique of tissue culture, or vegetative propagation, permits the regenerative cloning of whole plants by a procedure which does not require seeding, or sexual reproduction. In the procedure of the present invention, excised shoot apices are propagated in vitro in a sterile gel containing a nutrient medium along with plant growth hormones.

Any of a variety of basal nutrient media may be employed. While the one of choice is essentially that of Murashige and Skoog (identified below), others have been suggested by Skoog, Heller, Knog, Gamborg, White, and Street.

The basal medium usually contains (1) inorganic ions, both major and minor, required to maintain fluid balance and to act with certain enzymes, (2) energy sources, typically sucrose, which also provide a major source of carbon atoms for the formation of certain cell constituents, (3) nitrogen-containing compounds, mainly one or more amino acids, (4) essential vitamins and traces of certain metal ions, (5) plant growth hormones, as more fully developed below, and various other constituents.

The technique of tissue culture as a method of vegetative propagation has been elaborated upon in a number of the literature articles referred to earlier.

Fundamentally, the tissue culture protocol involves the removal of a part of the plant (explant) under sterile conditions, and placing it in an appropriate nutrient medium for growth. For cabbage, the preferred nutrient medium is an agar gel, which permits propagation under comparatively conservative techniques in order to avoid genetic alteration.

In the preferred approach, isolated shoot apices along with one or two leaf primordia, are excised from the selected inbred plants and are treated in a single stage tissue culture protocol. This stage combines plant shoot establishment, multiplication, and rooting. (A multiple stage protocol may alternatively be followed—i.e., culture establishment, multiplication, and rooting—but is not essential.)

Two hormones have been found especially useful for proper growth and development in culture. Auxins, which affect cell elongation, influence such processes as cell enlargement, leaf and organ separation, budding, flowering, fruit set and growth, and root initiation and development. The other group of hormones, cytokinins, influence the stimulation of cell division and proper formation and development of organs. A low auxin but high cytokinin content promotes to shoot development; a high auxin but low cytokinin content promotes root development.

For cabbage, the preferred protocol for vegetative propagation is to culture shoots from isolated shoot apices. This has been found to be effected best in a single stage agar-based nutrient medium that contains an auxin (e.g., 0.2–5.0 mg/l) and a cytokinin (e.g., 1–10 mg/l).

The shoots thus produced may be multiplied indefinitely or, if desired, can be stored. Cryogenic storage techniques have not yet been perfected for cabbage, but similar techniques have been used for other plant species; see Seibert U.S. Pat. No. 4,052,817, suggesting storage below minus 70° C. after controlled freezing and subsequent thawing. Seibert also suggests a variety of cryoprotectants. Optimally, storage at liquid nitrogen temperature is preferred.

After approximately three or four weeks, sufficient development of the shoots takes place to permit further propagation by multiplication in vitro, or the propagated shoots (plantlets) may be transplanted to greenhouse conditions for ultimate growth in the field to maturity. A hardening off treatment, consisting of maintaining the plantlets in a sterile (peat/vermiculite mixture) potting medium under conditions of mist and high humidity, prepares the plantlets for transplanting.

EXAMPLE (CABBAGE)

This Example reports the study of several hormonal and nutritional parameters influencing the in vitro development of excised shoot apices of head cabbage, *Brassica oleracea* L. var. *capitata*.

An in vitro culture protocol which ensures a capability of yielding normal plants from isolated shoot apices of this important vegetable crop has not been available. In vitro shoot apex culture or meristem culture has previously been employed to obtain pathogen-free plants (G. M. Morrel, *Amer. Orchid Soci. Bull.* 29, 495–497 (1960)), to asexually propagate plants (T. Murashige, M. N. Shabde, P. M. Hasegawa, F. H. Takatori, and J. B. Jones, *J. Amer. Soc. Hort. Sci.* 97, 158–161 (1972)), and to study morphogenic response of apical meristematic tissues (E. Ball, *Growth*, 24, 91–110 (1960), M. Shabde, and T. Murashige, "Hormonal requirements of excised *Dianthus caryophyllus* L. shoot apical meristem in vitro," *Amer. J. Bot.* 64, 443–448 (1977); H. S. Smith and T. Murashige, "In vitro development of the isolated shoot apical meristem of angiosperms," *Amer. J. Bot.*, 57, 562–568 (1970).)

Axillary buds were obtained from market mature field grown head cabbage, cultivar Golden Acre. Buds were disinfected by a 0.5–1.5 min. wash in 70–75% ethanol followed by soaking in 1% sodium hypochlorite for 7 min. and washing three times with sterile water. Shoot apices approximately 100–150 um in length were aseptically isolated from the axillary buds using microdissection. Each apex, or apical meristem, consisted of the apical dome with 1–2 subadjacent leaf primordia.

Apices were cultured on sterile 15 ml agar medium contained in $60 \times 15$ mm petri dishes or in 25 ml agar medium in $25 \times 150$ mm tubes. The basal nutrient medium contained the standard MS salt formulation (T. Murashige and F. Skoog, "A revised medium for the rapid growth and bioassays with tobacco tissue culture," *Physiol. Plant.*, 15, 473–497 (1962)) plus the following constituents, in mg/l: myo-inositol, 100; thiamine.HCl, 0.4; sucrose, 30,000; and agar, 7,000. The following were provided in the basal medium as test addenda: IAA (indole acetic acid) as the auxin, kinetin (6-furfurylaminopurine) as the cytokinin, sodium phosphate ($NaH_2PO_4.H_2O$), and adenine sulfate.

Ten to fifteen apices were used per treatment. Culture conditions were $26° \pm 2°$ C. and light at 2,500 lux from (Sylvania) cool white lamps 16 hrs/day. Culture period for observations was up to 6 weeks. Plants derived from culture were transplanted to a peat/vermiculite mixture after removing agar by washing with tap water. To harden the plants a mist system was used for the first two weeks. Plants were grown in a greenhouse ($80° \pm 4°$ C.) to market maturity (full head development).

Auxin and Cytokinin Interactions for Axillary Shoot Apex Development

For various other plant species it has been shown that isolated apices require auxins and/or cytokinins for continued development into plants (H. S. Smith and T. Murashige, "In vitro development of the isolated shoot apical meristem of angiosperms," Amer. J. Bot. 57, 562–568 (1970)). Therefore, experiments were carried out to investigate hormonal requirements for the development of cabbage shoot apices.

The variables studied, and the preferred nutrient composition that has been defined, are shown in Table A, below.

TABLE A

Culture Medium Composition for Plant Development from Isolated Shoot Apices of Cabbage

| INGREDIENTS | mg/l MEDIUM |
| --- | --- |
| Inorganic constituents | Murashige and Skoog, 1962 |
| Organic constituents | |
| myo-inositol | 100 |
| thiamine.HCl | 4 |
| sucrose | 30,000 |
| agar | 7,000 |
| pH | 5.7 |

| Variables Studied: | Recommended Amount |
| --- | --- |
| kinetin (0–10.0 mg/l) | 3 |
| IAA (0–10.0 mg/l) | 1 |
| adenine sulfate.2H$_2$O (80 mg/l) | Omit |
| NaH$_2$PO$_4$.H$_2$O (170 mg/l) | 170 |

Murashige, T., and F. Skoog, Physiol. Plant., 473–497, 15 (1962).

Initial studies determined the effect of IAA on shoot and leaf development from isolated cabbage apices with kinetin held constant at 3 mg/l (selected from preliminary experiments not described here). The results are shown in Table B. Optimal concentration of IAA for leaf induction was in the broad range of 0.1–10 mg/l, whereas IAA did not appear to influence the number of shoots differentiated.

TABLE B

Effect of IAA on In Vitro Development Shoot Apex of Cabbage

| IAA (mg/l) | Size of shoots (mm) | No of Leaves | No. of Shoots | No. of Roots |
| --- | --- | --- | --- | --- |
| 0 | 8 ± 2.5 | 1.6 ± 0.4 | 1.4 ± 0.5 | 0 |
| 0.1 | 13 ± 1.8 | 3.3 ± 0.7 | 2.3 ± 0.8 | 0 |
| 0.3 | 26 ± 6.8 | 3.4 ± 0.6 | 1.7 ± 0.2 | 0 |
| 1.0 | 19 ± 3.9 | 3.4 ± 0.6 | 1.8 ± 0.3 | 0 |
| 3.0 | 24 ± 2.8 | 3.3 ± 0.6 | 1.7 ± 0.2 | 0 |
| 10.00 | 23 ± 2.8 | 3.2 ± 0.7 | 2.0 ± 0.5 | 1.5 ± 1.3 |

Kinetin: 3 mg/l

In the next set of experiments, influence of kinetin concentrations on isolated cabbage apices was tested, with 1 mg/l IAA held constant. As can be seen in Table C, optimal kinetin concentration for both shoot and leaf development from isolated apices was 3 mg/l. Lower concentrations of kinetin (below 0.3 mg/l) caused callus formation and suppressed normal shoot development. This observation agrees with Shabde and Murashige's finding (M. Shabde, and T. Murashige, "Hormonal requirements of excised *Dianthus caryophyllus* L. shoot apical meristem in vitro," Amer. J. Bot. 64, 443–448 (1977)), which suggests that the isolated meristem dome of *Dianthus caryophylus* L. (carnation) requires both IAA and kinetin for its development into a plant.

TABLE C

Effect of Kinetin on In Vitro Development of Axillary Shoot Apex of Cabbage

| Kinetin | Size of Shoots (mm) | No. of Leaves | No. of Shoots | No. of Roots |
| --- | --- | --- | --- | --- |
| 0 | 2.1 ± 0.7 | 1.4 ± 0.4 | 0.6 ± 0.2 | 0 |
| 0.1 | 2.4 ± 0.3 | 1.8 ± 0.2 | 0.9 ± 0.1 | 0 |
| 0.3 | 5.1 ± 1.1 | 1.4 ± 0.2 | 0.6 ± 0.2 | 0 |
| 1 | 6.7 ± 1.2 | 1.7 ± 0.5 | 1.0 ± 0.2 | 0 |
| 3 | 27.8 ± 7.6 | 3.3 ± 0.5 | 2.5 ± 0.3 | 0 |
| 10 | 5.5 ± 0.5 | 2.0 ± 0.2 | 1.0 ± 0.1 | 0 |

IAA: 1 mg/l

Stimulation of Axillary Shoot Apex Development by Sodium Phosphate

Both adenine sulfate and sodium phosphate (monosodium form) have been employed in plant tissue culture medium as constituents to promote shoot organogenesis (T. Murashige, M. N. Shabde, P. M. Hasegawa, F. H. Takatori, and J. B. Jones, J. Amer. Soc. Hort. Sci. 97, 158–161, (1972)). Table D summarizes the effects of adenine sulfate and sodium phosphate in the presence of both IAA and kinetin on in vitro development of axillary shoot apices of cabbage.

TABLE D

EFFECT OF IAA, KINETIN, ADENINE SULFATE AND NaH$_2$PO$_4$ ON THE IN VITRO DEVELOPMENT OF AXILLARY SHOOT APEX OF CABBAGE

| Addenda* | Size of shoots (mm) | No. of Leaves | No. of shoots | No. of Roots |
| --- | --- | --- | --- | --- |
| Kinetin + IAA | 15 ± 1.6 | 2.4 ± 0.7 | 2 ± 0.6 | 0 |
| Kinetin + IAA + NaH$_2$PO$_4$ | 24.5 ± 6.6 | 4.5 ± 1.4 | 2.8 ± 0.5 | 4.5 ± 1.0 |
| Kinetin + IAA + Adenine Sulfate | 10.4 ± 3.8 | 3 ± 1.2 | 1.6 ± 0.6 | 0 |
| Kinetin + IAA + NaH$_2$PO$_4$ + Adenine Sulfate | 17 ± 3.1 | 2 ± 0.7 | 2 ± 0.4 | 0 |

*IAA (1 mg/l,) Kinetin (3 mg/l), Adenine Sulfate (80 mg/l), NaH$_2$PO$_4$ (212 mg/l) were provided in the basal medium.

Adenine sulfate at 80 mg/l repressed shoot initiation and inhibited the chlorophyllous coloration in leaves. Murashige et al. (T. Murashige, M. N. Shabde, P. M. Hasegawa, F. H. Takatori, and J. B. Jones, J. Amer. Soc. Hort. Sci. 97, 158–161 (1972)) reported that 160 mg/l adenine sulfate was toxic to asparagus shoot apex development. Thus, adenine sulfate was excluded from the medium components for cabbage apex culture. In contrast, sodium phosphate at 170 mg/l promoted apex development and rooting. Rooting response in media containing sodium phosphate may be related to the enhanced vigor of the developing shoots.

Establishing Mature Cabbage Plants Derived from In Vitro Axillary Shoot Apices Using the medium presented in Table E, at least 70% of excised cabbage apices developed into plants. A separate rooting step was usually not necessary. However, the rate of root development was enhanced by transferring shoots at 4 weeks to the same medium minus kinetin. After two weeks on the minus kinetin medium the developing plants were transplanted to pots containing a peat/vermiculite mixture and kept in a greenhouse. Survival at the transplanting stage was more than 90% under the conditions described.

TABLE E

Culture Medium Composition for Plant Development from Isolated Axillary Shoot Apices of Cabbage[a]

| CONSTITUENTS | mg/l |
| --- | --- |
| Inorganic Salts | |
| MS Salts formulation | [b] |
| $NaH_2PO_4.H_2O$ | 170 |
| Organic Substances | |
| Myo-inositol | 100 |
| Thiamine.HCl | 0.4 |
| Kinetin | 3 |
| IAA | 1 |
| Sucrose | 30,000 |
| Complex Addenda | |
| Agar (SIGMA grade) | 7,000 |

[a] pH of medium was adjusted to 5.7 with 0.1 N KOH and/or 0.1 N HCl before autoclaving.
[b] Murashige and Skoog (T. Murashige and F. Skoog, "A revised medium for the rapid growth and bioassays with tobacco tissue culture," Physiol. Plant., 473–497 (1962)).

The developmental sequence from a shoot apex to a greenhouse transplant has been studied. After 1–2 weeks the shoot apex started to swell, and elongation of several chlorophyllous leaf primordia was observed. Further apex development continues up to 4–5 weeks. Occasionally, formation of adventitious shoots from the developing apex was apparent. After four weeks, several roots were generated from the basal portion of shoots. After two months under greenhouse conditions, plants developed normal heads. The plants derived using this method were morphologically uniform; the genetic variability of plants cloned by this method has not yet been examined at the chromosomal level.

The foregoing Example demonstrated that, in cabbage, the presence of both IAA and kinetin are necessary for development of organized shoots within 6 weeks. At low concentrations of kinetin (below 0.3 mg/l) in medium containing IAA, callus formation was observed and normal shoot development was suppressed. The optimum response range for IAA was quite broad (0.3–10.0 mg/l) whereas that for kinetin was narrow (3.0 mg/l). Adenine sulfate does not appear to be a beneficial media component and it appears to repress the rooting response. Sodium phosphate on the other hand promotes apex development and rooting. (Rooting response in media containing sodium phosphate may be related to the enhanced vigor of the developing shoots.) A separate rooting step was not necessary in the media shown in Table E: however, the rate of root induction was enhanced if shoots at 4 weeks were transferred to the same medium minus kinetin. After two weeks the developing plants were ready for transplanting to the greenhouse. Survival at the transplanting stage was quite high if moisture and humidity were high initially.

We claim:

1. A process for the production of high purity hybrid cabbage seed, comprising:
    (a) selecting a maximally self-incompatible parent plant;
    (b) cloning said selected maximally self-incompatible parent plant by axillary bud propagation to produce a first cloned parental line that is both maximally self-incompatible and maximally sib-incompatible;
    (c) crossing plants of said first cloned parental line with plants of a second parental line; and
    (d) collecting high purity hybrid seed from said first cloned parental line,
wherein said axillary bud propagation is effected by establishing shoots from an excised axillary bud from said selected maximally self-incompatible parent plant, multiplying said shoots by axillary buds excised from said shoots, and rooting axillary buds excised from said multiplied shoots.

2. The process according to claim 1 wherein said second parental line is obtained by axillary bud propagation of a second maximally self-incompatible parent plant to produce a second cloned parental line that is both maximally self-incompatible and maximally sib-incompatible, wherein said axillary bud propagation is effected by establishing shoots from an excised axillary bud from said second maximally self-incompatible parent plant, multiplying said shoots by axillary buds excised from said shoots, and rooting axillary buds excised from said multiplied shoots, and wherein the hybrid seeds are collected from the plants of either or both cloned parental lines.

* * * * *

UNITED STATES PATENT AND TRADEMARK OFFICE
CERTIFICATE OF CORRECTION

PATENT NO. : 4,381,624

DATED : May 3, 1983

INVENTOR(S) : Robert H. Lawrence, Jr. and Phillip E. Hill

It is certified that error appears in the above-identified patent and that said Letters Patent is hereby corrected as shown below:

Column 3, line 27, "Stottlemeyer" should read -- Stottlemyer --.
Column 5, line 17, "Knog" should read -- Knot --.

Signed and Sealed this

Twenty-third Day of August 1983

[SEAL]

Attest:

GERALD J. MOSSINGHOFF

Attesting Officer  Commissioner of Patents and Trademarks